(12) United States Patent
Tyagi et al.

(10) Patent No.: US 10,454,867 B2
(45) Date of Patent: Oct. 22, 2019

(54) ENHANCED E-MAIL DELIVERY TO MOBILE DEVICES

(71) Applicant: AIRWATCH LLC, Atlanta, GA (US)

(72) Inventors: Subham Kumar Tyagi, J.P. Nagar (IN); Sriparna Chakraborty, Bangalore (IN); Dheeraj Bhati, Bangalore (IN)

(73) Assignee: AIRWATCH LLC, Atlanta, GA (US)

( * ) Notice: Subject to any disclaimer, the term of this patent is extended or adjusted under 35 U.S.C. 154(b) by 157 days.

(21) Appl. No.: 15/018,875

(22) Filed: Feb. 9, 2016

(65) Prior Publication Data

US 2017/0142048 A1 May 18, 2017

(30) Foreign Application Priority Data

Nov. 17, 2015 (IN) .............................. 619/CHE/2015

(51) Int. Cl.
*H04L 12/58* (2006.01)
*H04W 52/02* (2009.01)

(52) U.S. Cl.
CPC ......... *H04L 51/12* (2013.01); *H04W 52/0212* (2013.01); *H04W 52/0258* (2013.01); *H04W 52/0261* (2013.01); *H04W 52/0251* (2013.01); *Y02D 70/00* (2018.01); *Y02D 70/142* (2018.01)

(58) Field of Classification Search
CPC .............. H04L 51/12; H04W 52/0212; H04W 52/0258; H04W 52/0261; H04W 52/0251; Y02B 60/50
See application file for complete search history.

(56) References Cited

U.S. PATENT DOCUMENTS

| | | | | |
|---|---|---|---|---|
| 8,166,164 B1 * | 4/2012 | Luna | ...................... | H04L 67/22 709/203 |
| 10,088,890 B1 * | 10/2018 | Ehrhardt | ............... | G06F 1/3287 |
| 2001/0007140 A1 * | 7/2001 | Landry | ................. | G06F 11/327 714/48 |
| 2004/0054569 A1 * | 3/2004 | Pombo | ............... | G06Q 10/0633 705/7.27 |
| 2005/0066006 A1 * | 3/2005 | Fleck | .................... | G06F 1/3203 709/206 |
| 2007/0229350 A1 * | 10/2007 | Scalisi | .................... | G06F 21/35 342/350 |
| 2007/0264948 A1 * | 11/2007 | Jansson | ................. | G06F 1/3203 455/127.5 |
| 2007/0266106 A1 * | 11/2007 | Kato | .................... | H04M 1/663 709/206 |

(Continued)

*Primary Examiner* — Blake J Rubin
(74) *Attorney, Agent, or Firm* — Clayton McKay & Bailey, PC

(57) ABSTRACT

Systems and methods for providing e-mail to a mobile client are disclosed. In one example, the method can include receiving, at a server associated with transmitting e-mail to the mobile client, an indication of a battery level in the mobile client. The method can also include comparing the battery level to a threshold level and synchronizing e-mail with the mobile client when the battery level meets the threshold level. The method can further include activating, when the battery level is below the threshold level, a filtered mode for synchronizing e-mail with the mobile client, the filtered mode transmitting fewer than all of the available e-mail messages for the mobile client.

14 Claims, 7 Drawing Sheets

(56) References Cited

U.S. PATENT DOCUMENTS

| | | | |
|---|---|---|---|
| 2008/0065734 A1* | 3/2008 | Yu | H04L 51/24 709/206 |
| 2008/0215684 A1* | 9/2008 | Thorkelsson | H04L 12/66 709/206 |
| 2008/0301250 A1* | 12/2008 | Hardy | G06Q 10/107 709/207 |
| 2009/0149203 A1* | 6/2009 | Backholm | H04L 51/12 455/466 |
| 2009/0164586 A1* | 6/2009 | Douglas | H04L 51/24 709/206 |
| 2010/0042691 A1* | 2/2010 | Maguire | G06F 1/3203 709/206 |
| 2010/0042693 A1* | 2/2010 | Eriksson | H04L 51/24 709/206 |
| 2010/0093381 A1* | 4/2010 | Maguire | G06Q 10/107 455/466 |
| 2010/0115259 A1* | 5/2010 | Elsila | G06F 1/3203 713/100 |
| 2010/0115314 A1* | 5/2010 | Sultenfuss | G06F 1/3203 713/323 |
| 2010/0274507 A1* | 10/2010 | Black | H04W 36/385 702/63 |
| 2011/0125856 A1* | 5/2011 | Chu | H04M 1/72552 709/206 |
| 2011/0173681 A1* | 7/2011 | Qureshi | H04L 63/0823 726/4 |
| 2012/0143959 A1* | 6/2012 | Wang | H04L 51/063 709/206 |
| 2012/0221651 A1* | 8/2012 | Rabii | H04L 51/38 709/206 |
| 2012/0239949 A1* | 9/2012 | Kalyanasundaram | G06F 1/3212 713/320 |
| 2012/0278620 A1* | 11/2012 | Singh | H04L 51/063 713/168 |
| 2012/0303774 A1* | 11/2012 | Wilson | H04L 67/26 709/206 |
| 2013/0019116 A1* | 1/2013 | Ochi | G06F 1/3284 713/323 |
| 2013/0059570 A1* | 3/2013 | Hara | H04L 67/24 455/414.1 |
| 2013/0198398 A1* | 8/2013 | Parker | H04L 65/1069 709/228 |
| 2014/0210620 A1* | 7/2014 | Snodgrass | G08B 21/245 340/539.17 |
| 2014/0366042 A1* | 12/2014 | Chan | G06F 9/4825 719/318 |
| 2015/0296049 A1* | 10/2015 | Green | G06Q 10/107 709/206 |
| 2015/0350807 A1* | 12/2015 | Andrews | H04W 76/14 455/414.2 |
| 2016/0014057 A1* | 1/2016 | Gudla | H04L 63/08 709/206 |
| 2016/0241657 A1* | 8/2016 | Amrhein | H04L 67/26 |
| 2016/0316314 A1* | 10/2016 | Swaminathan | H04W 4/008 |
| 2016/0360489 A1* | 12/2016 | Boodannavar | H04B 7/0413 |
| 2017/0094638 A1* | 3/2017 | Borges | H04L 67/322 |

\* cited by examiner

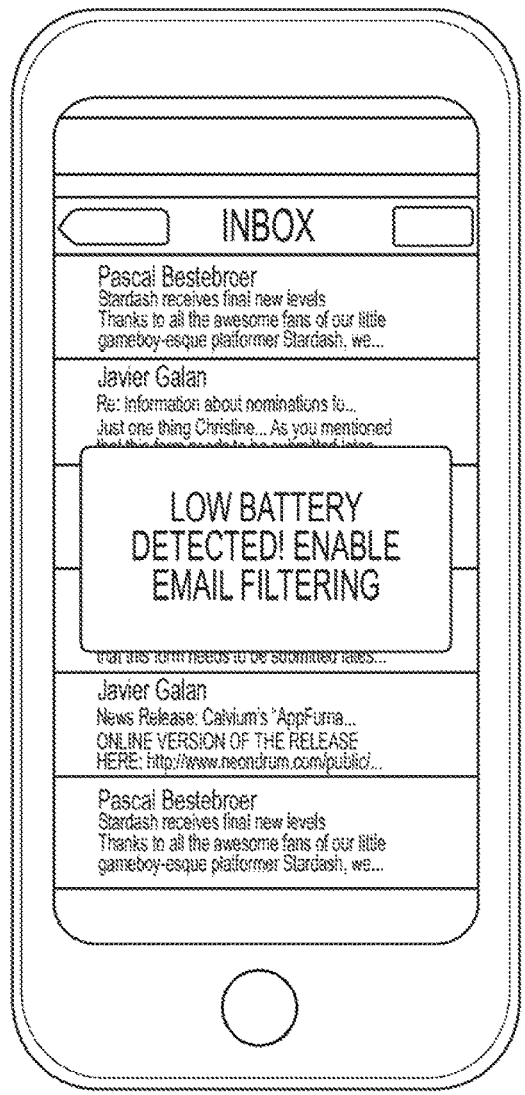
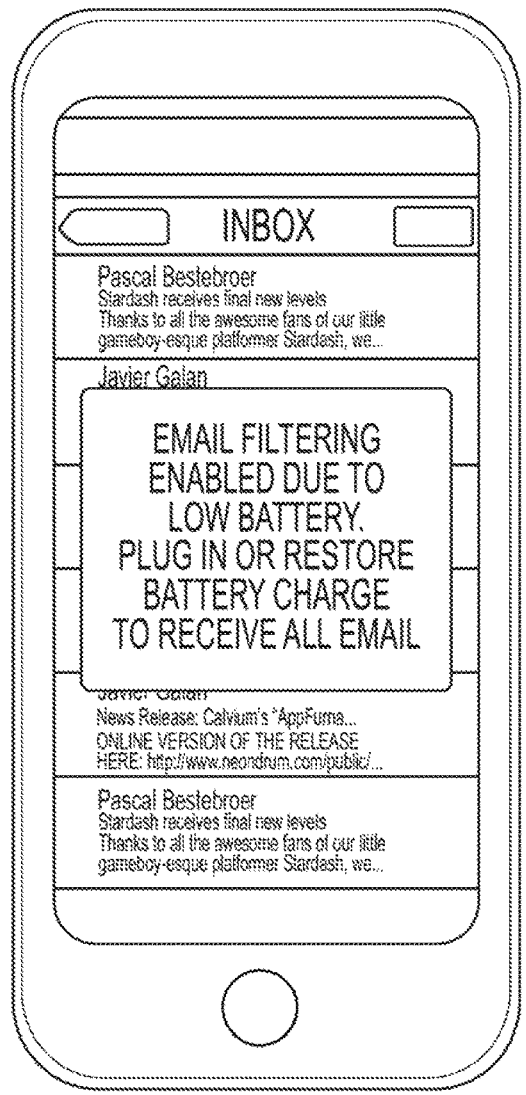
*FIG. 5A*  *FIG. 5B*

ENHANCED E-MAIL DELIVERY TO MOBILE DEVICES

CROSS-REFERENCE TO RELATED APPLICATIONS

Benefit is claimed under 35 U.S.C. 119(a)-(d) to Foreign application Serial No. 6196/CHE/2015 filed in India entitled "ENHANCED E-MAIL DELIVERY TO MOBILE DEVICES", on Nov. 17, 2015, by AIRWATCH LLC, which is herein incorporated in its entirety by reference for all purposes

BACKGROUND

The number of e-mails that users send and receive continues to rise. Receiving large numbers of e-mails throughout the day on a mobile device can distract users from accomplishing other tasks because many of those e-mails are of little importance. In addition, receiving e-mails from a server can drain a mobile device's battery.

One way for a mobile device to receive new e-mails involves having an e-mail client periodically poll an e-mail server. This process involves opening a socket connection that will remain open until the server responds. If new messages have arrived, the server indicates that the mail folders have changed, causing the e-mail client to initiate a synchronization command with the server. In response, all of the new messages are sent to the mobile device. This process of opening a connection, keeping the connection open, requesting synchronization, and downloading new messages consumes data traffic, battery life, and a user's attention. In addition, the periodic polling can occur even when a device is in sleep mode. The device can transition from a sleep or low power state to an active mode to contact the e-mail server and check for new messages. This process ensures that e-mail has been synchronized when a user checks the mobile device, but consumes battery life even when the device is not being used. Even in push systems where the server sends a notification to the e-mail client upon receipt of a new e-mail for a user, the act of synchronizing e-mails with the mobile device still consumes considerable battery life.

In some situations, consumption of battery life might not have considerable importance, such as when the user has their mobile device plugged in and charging or when the battery is sufficiently charged. However, once the battery life approaches a lower level, the user may want to conserve battery life to ensure that the mobile device is available for important tasks.

In addition to conserving battery life, the act of viewing a screen and reading or deleting unimportant e-mail can distract a user from accomplishing other tasks. Many e-mails that a user receives do not need to be read or responded to, yet modern e-mail systems continue to send all e-mails to a mobile device and provide only coarse methods for filtering "spam" e-mail.

Based on at least these problems in the technology, needs exist for filtering messages sent to a mobile device and conserving battery life.

SUMMARY

Systems, methods, and computer-readable media for delivering e-mail to a mobile client are disclosed. In one example, the method can include receiving, at a server associated with transmitting e-mail to the mobile client, an indication of a battery level in the mobile client. The method can also include comparing the battery level to a threshold level and synchronizing e-mail with the mobile client when the battery level meets the threshold level. The method can further include activating, when the battery level is below the threshold level, a filtered mode for synchronizing e-mail with the mobile client, the filtered mode transmitting fewer than all of the available e-mail messages for the mobile client.

It is to be understood that both the foregoing general description and the following detailed description are exemplary and explanatory only and are not restrictive of the examples, as claimed.

BRIEF DESCRIPTION OF THE DRAWINGS

FIGS. 5A and 5B are exemplary user interfaces for e-mail clients.

DESCRIPTION OF THE EXAMPLES

Figure 1:
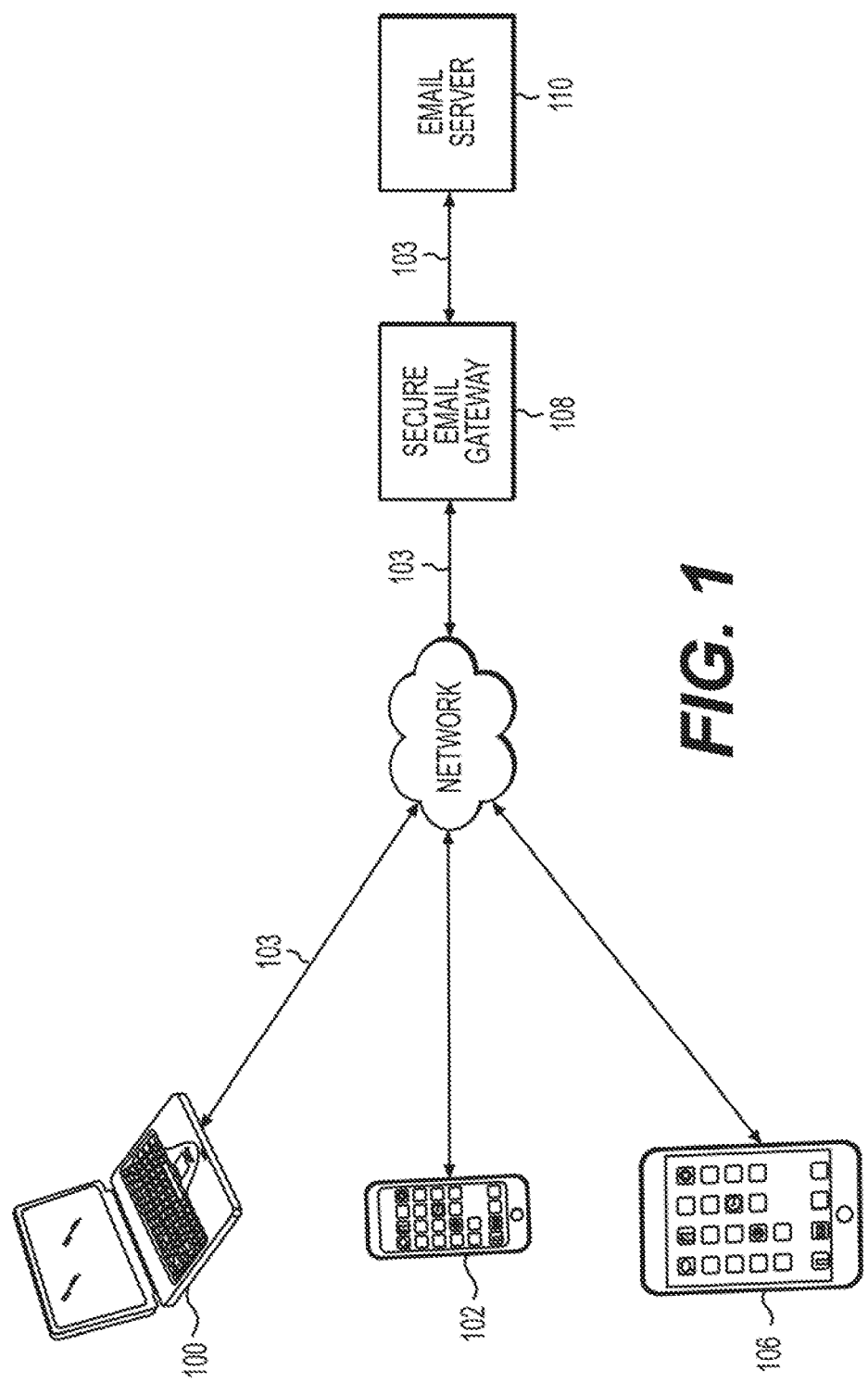
FIG. 1 is an exemplary system for transmitting e-mail to mobile devices.

Systems and methods consistent with the disclosure can adjust the timing and characteristics of e-mail delivery to mobile devices to conserve battery life and minimize user distractions. In one example, an e-mail gateway, instead of the mobile device, can periodically poll an e-mail server to determine if any new messages exist in a user's folders. If new messages do exist, a notification can be sent to the mobile device using cloud messaging. In response, the mobile device can initiate a synchronization event with the e-mail server through the e-mail gateway. As a result, the mobile client need not open a socket connection periodically to check for new messages waiting on the e-mail server, and instead can contact the server in response to a notification indicating new messages have arrived. In some embodiments, the e-mail gateway that polls the e-mail server for new messages can be part of the e-mail server itself.

In addition, the mobile device can be configured to provide an indication of remaining battery life to the e-mail gateway. As the battery life of a mobile device drops below a defined threshold, such as fifteen percent, the mobile device can notify the e-mail gateway or e-mail server of a low-battery condition. In response, enhanced filtering can be engaged to reduce the number of e-mails that are sent to the mobile device. In one example, the e-mail gateway can continue to receive messages from the e-mail server as new messages arrive. However, the e-mail gateway can filter messages and only transmit messages that meet defined characteristics to the mobile devices. When the mobile device is connected to a battery charging station or when the battery level exceeds the defined threshold, the e-mail gateway can then initiate a full synchronization with the mobile device and provide the messages that were temporarily withheld from the mobile device due to the low battery condition.

Because a user may have multiple mobile devices, the e-mail gateway can also track the messages that have been sent to a user's mobile devices and coordinate synchronization. For example, a user can have a laptop connected to a docking station that is at full battery life, a mobile smartphone, and a mobile tablet. These devices can have local copies of mailboxes that are all associated with the same e-mail account, such as a user's corporate e-mail. When the battery life of the user's mobile smartphone drops below the defined threshold, the e-mail gateway can filter and reduce the number of messages sent to the mobile smartphone. The mobile smartphone can receive a notification that it will be receiving a reduced set of filtered e-mails while battery life remains low. In some embodiments, the user can be given an option to override message filtering. Meanwhile, the user's laptop and mobile tablet can continue receiving all e-mails without regarding to the filtering process. Once the mobile smartphone is plugged in or resumes sufficient battery life, the e-mail gateway can synchronize with the smartphone so that the user's inbox and other folders correlate between the smartphone, tablet, laptop, and any other device used to check e-mail.

FIG. 1 illustrates an exemplary system for delivering e-mail to mobile devices. A plurality of mobile devices including a laptop 100, a cell phone 102, and a tablet 106 can be associated with a particular user and their e-mail account. Although not illustrated, the system can manage mobile devices 100, 102, 106 associated with many users, along with e-mail clients installed on desktops or other workstations. The desktops, workstations, and other devices can be connected with the e-mail server 110 directly over a secure corporate network or through the secure e-mail gateway 108.

The mobile devices 100, 102, 106, secure e-mail gateway 108, and e-mail server 110 can communicate over one or more network connections 103. The network connections 103 can include, for example, wired or wireless connections such as the Internet, a local area network, a workstation peer-to-peer network, a direct link network, a cellular network, or any other suitable communication platform. Firewalls and other security mechanisms can exist between the mobile devices using a public network, such as a cellular network or public Wi-Fi network, and the secure e-mail gateway 108 and e-mail server 110.

The secure e-mail gateway 108 can provide an interface for accessing e-mail server 110. The secure e-mail gateway 108 can enhance security by requiring that the mobile devices 100, 102, 106 comply with different policies that can be established by a system administrator. For example, the mobile devices can be required to enroll with enterprise mobility management software, to not have a jailbroken or rooted status, to have a valid certificate relating to being managed, to have been encrypted, to use a secure e-mail client instead of a native or web-based e-mail client, to automatically employ a virtual private network (VPN) connection when accessing corporate resources, and other configurations that enhance security of access to corporate resources. Additional examples include requiring a minimum passcode length on the mobile device, and restricting use of copy/paste to avoid material being copied from a secure e-mail client into other unapproved applications.

The mobile devices can enroll with enterprise mobility management software and receive a secure e-mail client that can be used to access e-mail through the secure e-mail gateway 108. For example, communications between the managed e-mail clients and the secure e-mail gateway 108 can be encrypted using FIPS 140/AES 256-bit encryption, and e-mail stored at rest on the mobile devices, secure e-mail gateway 108, and e-mail server 110 can also be encrypted. As additional examples, the mobile clients can be restricted from transmitting attachments, restrict attachments of a given size, restrict opening attachments into only approved applications, and disable certain HTML content to prevent unintended installation of malware. As another example, an administrator can define a policy that prevents e-mail forwarding from the secure e-mail client to blacklisted domains.

The secure e-mail gateway 108 can periodically poll the e-mail server 110 to determine if there have been any changes to user's e-mail folders. One example of a change includes arrival of a new e-mail in the user's inbox. The secure e-mail gateway can employ different modes of operation depending on the battery life for each mobile device associated with a user. One exemplary mode includes normal operation during which all e-mail can be sent to the mobile devices as the e-mail arrives at e-mail server 110. In this mode, a user's inbox as seen on a mobile device 100, 102, or 106 can be the same as an inbox on, for example, the user's desktop or workstation. The secure e-mail gateway 108 may not, in one example, separately store e-mail when all of a user's devices are executing in a normal operational mode.

In a second exemplary mode, the secure e-mail gateway 108 can operate to conserve battery life of a mobile device. In this mode, the secure e-mail gateway 108 can filter and transmit a reduced set of e-mails to the user's mobile devices which have a low battery condition. Messages that are filtered can be temporarily stored by the secure e-mail gateway 108 so that the messages can be synchronized with a mobile device once it resumes adequate battery life or a charging status. The transition between the normal operational mode and the battery saving mode can be based on battery life notifications received from the mobile devices and will be described in more detail below.

E-mail server 110 can operate as an e-mail server that sends, receives, and stores e-mail for a plurality of users. For example, e-mail server 110 can be a MICROSOFT EXCHANGE server. Although illustrated as separate devices, secure e-mail gateway 108 and e-mail server 110 can exist within a single computing device, and the functionality provided by secure e-mail gateway 108 can be implemented using software executing on the e-mail server 110.

The components in FIG. 1, including laptop 100, cell phone 102, tablet 106, secure e-mail gateway 108, and e-mail server 110 can be computing systems that include one or more hardware or software components configured to execute software programs, such as software for managing mobile devices to provide secure access to corporate resources, including e-mail. For example, the computing system can include one or more processors, memory (e.g., RAM, ROM, hard drives, databases), input/output (I/O) modules for communicating with connected or network devices, and various interfaces, such as a keyboard, camera, mouse, and touch-screen. The computing systems can also include a computer-readable medium including computer-executable instructions for performing methods consistent with certain disclosed examples. The servers can also be distributed systems using multiple processors and memory units, and can include or connect to cloud-based storage systems.

Figure 2:
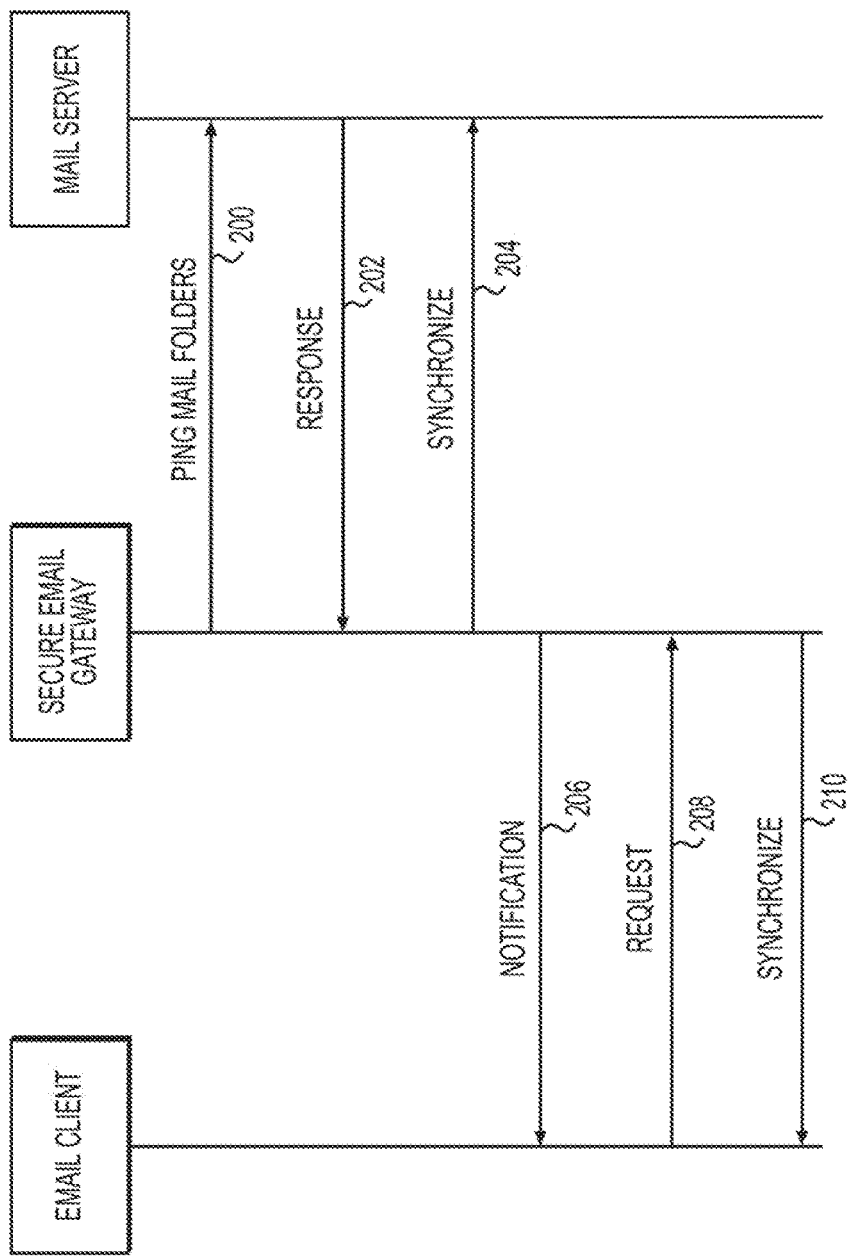
FIG. 2 is an exemplary sequence diagram for transmitting e-mail to mobile devices.

FIG. 2 is an exemplary sequence diagram for transmitting e-mail to mobile devices. Beginning at step 200, the secure e-mail gateway can poll the mail server to check for any new messages associated with a user's account. The mail server responds at step 202 by indicating the presence or absence of new messages. For example, the mail server can respond by indicating that there has been a change to a folder for a particular user, which can indicate that a new message has arrived. Alternatively, the mail server can push a notification to the secure e-mail gateway when a new message arrives, instead of using a polling and response process.

If the mail server indicates that there has been a change to a folder, at step 204, the secure e-mail gateway can synchronize messages with the mail server. For example, the mail server can send any new messages to the secure e-mail gateway, the secure e-mail gateway can notify the mail server that certain messages have been moved or deleted, and other synchronization functions can occur. In one example, the secure e-mail gateway receives only new messages that have arrived at the mail server and have not yet been transmitted to the e-mail client. In another example, the functionality of the secure e-mail gateway can be integrated with the mail server.

When synchronization results in the secure e-mail gateway obtaining messages that have not yet been sent to the e-mail client, the secure e-mail gateway can send a notification to the e-mail client at step 206. The notification can be sent as part of a push protocol using a variety of cloud messaging services, which can vary depending on the operating system of a device. For example, e-mail clients executing on a mobile device using ANDROID may use the GOOGLE cloud messaging service, whereas mobile devices using the iOS operating system can use the APPLE push notification service. The e-mail client 206 receives the notification and determines that it should contact the secure e-mail gateway or mail server.

At step 208, the e-mail client sends a request to the e-mail gateway. The secure e-mail gateway synchronizes messages with the e-mail client at step 210. As a result, the e-mail client receives new e-mail messages that have arrived at the mail server without having to periodically poll the mail server for messages. Alternatively, the e-mail client can synchronize messages directly with the mail server using a socket connection after receiving a notification through a cloud messaging service.

Figure 3:
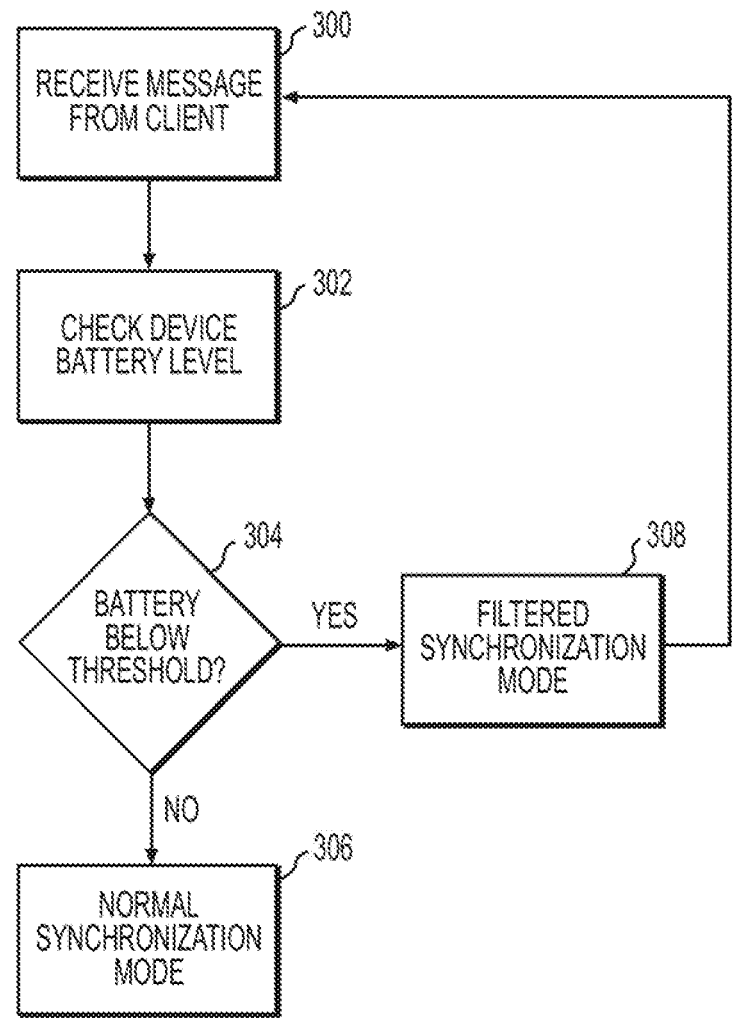
FIG. 3 is an exemplary flowchart for determining an operational mode for transmitting e-mail to mobile devices.

FIG. 3 is an exemplary flowchart for determining an operational mode for transmitting e-mail to mobile devices. The e-mail client can notify the secure e-mail gateway or mail server when its battery level has reached a predefined level. As a result, the secure e-mail gateway can reduce the number of e-mail messages that will trigger a notification to the e-mail client, and, in turn, reduce the number of synchronization events with an e-mail client. This conserves battery life for a user when the battery life has reached a predefined level. Alternatively, a user can engage a filtered synchronization mode even without regard to battery life to reduce distractions or for other reasons. For example, a user can engage a filtered mode upon entering a meeting to reduce the number of distractions during a meeting.

At step 300, the secure e-mail gateway can receive a message from the e-mail client that contains device battery level information or a command to engage filtered e-mail mode. The message can include, for example, a device identifier such as a universally unique identifier (UUID), an account identifier, and a battery life. The battery life can be obtained from the operating system executing the e-mail client using application program interface calls. The account identifier can identify the user's mail account on the mail server. The device identifier can identify the device which is providing its battery life. In this way, the secure e-mail gateway can track a plurality of different devices for a particular user's e-mail account, and only engage the filtered mode of operation for particular devices having a low battery condition.

As an example, a user can have a tablet, a laptop, and a smartphone. All three devices can be configured to access the user's mail account and receive e-mail. When the battery life for a particular device, such as the tablet, drops below a threshold level, the secure e-mail gateway can engage a filtered e-mail synchronization mode with respect to the tablet, but not the user's laptop and smartphone. The secure e-mail gateway can distinguish between the devices based on the device identifier included with the message at step 300.

The client device can send the message at step 300 through a variety of different channels and at different times. For example, the client device can send the message with each request sent in response to receiving a notification from the secure e-mail gateway, on its own when a device's battery life drops below a defined level, or in response to a request from a user to engage a filtered mode.

At step 302, the secure e-mail gateway can check the device's battery level included in the message. The secure e-mail gateway can store a predefined level, such as fifteen percent, and determine whether battery level has reached or fallen below that predefined level at step 304. In other examples, the mobile device can check the battery level itself, and send a message to the secure e-mail gateway that indicates whether the battery level is low or high. The particular battery level that is considered low or high can be defined by a user of the mobile device or by a system administrator.

If the battery level is below the threshold, the secure e-mail gateway can engage filtered synchronization mode at step 308, as described in more detail below. If the battery level exceeds the threshold, the secure e-mail gateway can use a normal synchronization mode at step 306 during which all messages can be synchronized with the mobile client. In some examples, the mobile client can override a filtered synchronization mode. For example, prior to entering a filtered synchronization mode, the mobile client can prompt a user to determine if the user would like to engage filtered synchronization mode. A user can decline to enter a filtered synchronization mode even when the battery life is below a threshold. As an example, a user might know that they will be able to charge their device before the device's battery life becomes completely drained, and therefore may want to maintain a normal synchronization mode. In this example, the mobile device can send the message to the secure e-mail gateway with either an arbitrarily high battery life, such as one-hundred percent, or send the actual battery life with a flag indicating that the user does not wish to engage filtered synchronization mode.

Figure 4:
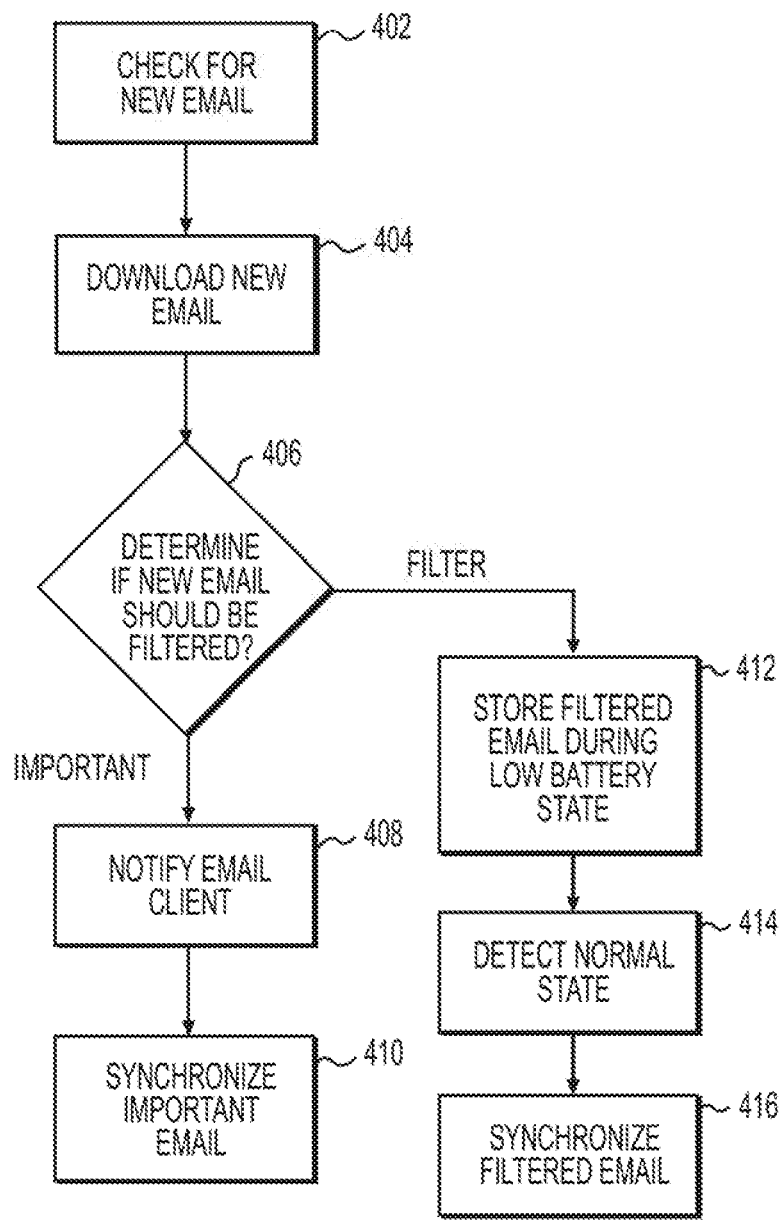
FIG. 4 is an exemplary flowchart for filtering e-mail.

FIG. 4 is an exemplary flowchart for filtering and delivering e-mail during a filtered synchronization mode. In one example, the steps of FIG. 4 can be performed by the secure e-mail gateway in response to synchronizing e-mail with the mail server. At steps 402 and 404, the secure e-mail gateway can check for new e-mail and download the new e-mail from the mail server as described previously.

At step 406, the secure e-mail gateway determines whether a particular new e-mail should be filtered. E-mails can be filtered based on a number of different factors, including the sender of the message, whether the message has been marked as important, the type of message (e.g., a message providing or cancelling a meeting invite), the timing for sending the message, whether the message is a response to a prior message sent by the user, whether the message is sent to only a particular user, to multiple users, or to a distribution list, whether the user is included in the to line or the cc line, keywords within the subject or body, and other factors. Users can also define a whitelist and rules for messages that should always be delivered. For example, a user can indicate that all messages sent from their manager should be delivered. In addition, the secure e-mail gateway can utilize machine learning to track user interaction and improve the filtering process over time, as described below.

If the particular message should be filtered, the secure e-mail gateway can store filtered e-mail during the low battery state at step 412. The secure e-mail gateway can proceed with synchronizing messages with other user devices that do not currently have a low battery state. The secure e-mail gateway can store an indication of which devices have been filtered verse synchronized using, for example, a device identifier.

At step 414, the secure e-mail gateway can detect a normal state by receiving a message from the client device when the battery life has returned to normal, when the client device has been plugged in to charge, or when the user has selected to override the filtering mode. Next, at step 416, the secure e-mail gateway can synchronize e-mail with any of the user's devices that were placed in a filtering mode.

If the secure e-mail gateway determines that a particular new e-mail message is important and therefore should not be filtered, at step 408, the secure e-mail gateway can notify the mobile device that a new message has arrived.

The mobile device can then synchronize with the secure e-mail gateway at step 410 to receive important new messages and should not be filtered. The mobile device therefore receives a reduce set of available new messages when filtering has been engaged, which conserves battery life of the mobile device.

FIGS. 5A and 5B illustrate exemplary user interfaces for e-mail clients. As shown in FIG. 5A, a user can receive a notification that the device has a low battery state, and that e-mail filtering will be enabled. The user can choose to override e-mail filtering if desired. In FIG. 5B, the user can be notified that e-mail filtering has been enabled due to a low battery state, and that normal e-mail synchronization can resume when the mobile device is plugged in or its battery charge is otherwise restored. Although not illustrated, the user can also receive a notification that normal synchronization has been resumed and filtering disabled once the device is plugged in or battery life is restored.

Figure 6:
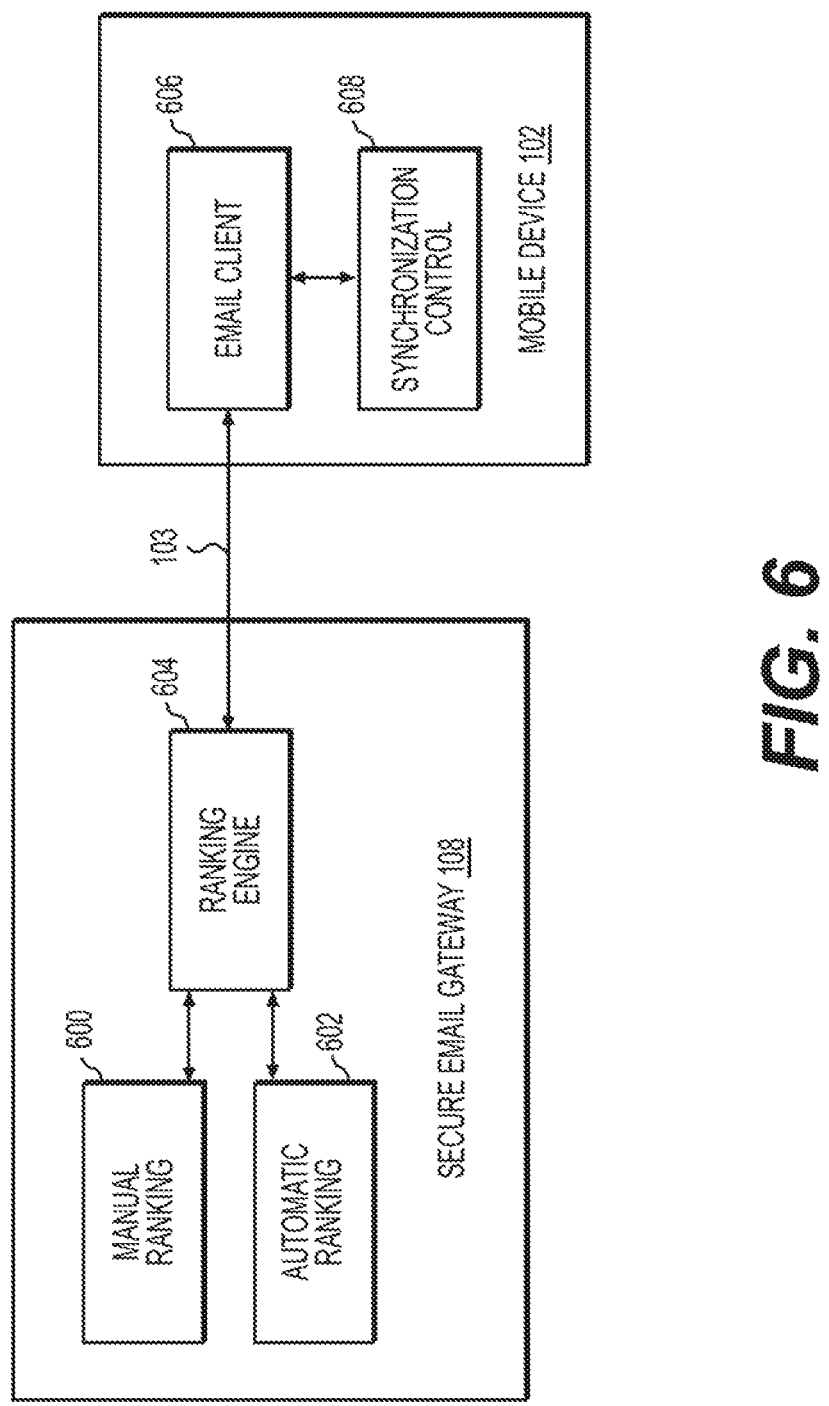
FIG. 6 is an exemplary system for filtering e-mail.

FIG. 6 is an exemplary system for filtering e-mail. Although described herein as filtering e-mail based on a low-battery state, e-mail filtering can also be enabled in a variety of other situations. For example, the system can enable filtering while a mobile device is roaming, when the user enters an important meeting, when the mobile device is in a defined geographic area, or in other situations.

The secure e-mail gateway 108 can filter e-mail based on factors defined by a user 600, factors determined automatically by the system 602, or a combination of manual rankings and automatic rankings. A ranking engine 604 executing on the secure e-mail gateway can rank, for each received e-mail, its importance to determine whether the e-mail should be delivered to the e-mail client 606 during filtered execution mode. In addition, the mobile device 102 can execute a synchronization control module 608. The synchronization control module 608 can monitor user interactions with e-mail and provide feedback to the automatic ranking module 602, as described below. The synchronization control module 608 can also provide a user interface through which a user can manually rank the importance of certain factors.

Examples of manual rankings 600 can include any factors established by a user or system administrator. For example, when the sender of a message includes the user's manager or assistant, the message would be more likely to be delivered during filtered mode. Message senders that do not exist in a user's contacts could be more likely to be filtered. The user or administrator could also define blacklists that should not be included in filtered messages. For example, a user might subscribe to several news services that provide daily or weekly e-mails and can be filtered to conserve battery life or reduce user distractions.

Examples of automatic rankings 602 can include factors that are automatically determined based on system interaction and analysis. The synchronization control module 608 can monitor how long a user views a particular e-mail on their mobile device. Based on the duration, e-mail messages that a user tends to view for a longer period of time or archive for future reference can be identified as having a higher importance. For example, future responses to the same message chain can be marked as more important, future messages from the same sender can be marked as important, and keywords in the body or subject can be extracted and used to rank messages more highly. If a user deletes a message without viewing it, messages from that sender, or in response to that e-mail thread, can be marked with lower importance. Similarly, if a user frequently deletes messages sent to a particular distribution list on which the user is included, then messages sent to that mailing list can have reduced importance and become more likely to be filtered. In this way, the system can continually improve upon and learn which e-mails should be filtered based on user interactions.

The ranking engine 604 can evaluate a number of different factors to determine whether to filter e-mail. The number of times that messages having similar characteristics are archived, read, opened and deleted, or deleted without being read can be tracked to improve the ranking engine's decision making. The actions that a particular user takes with regard to a delivered e-mail can be tracked using a message identifier, and the ranking engine 604 can receive from the mobile device 102 the message identifier and information regarding how the user interacted with the message (e.g., deleted without reading, forwarded to other users, or replied to). The ranking engine can then open and analyze the message using the message identifier, and modify its learning algorithm based on the user interactions, keywords it identifies in the e-mail message, and the other exemplary described factors. In one example, the ranking engine can implement a neural network to rank particular e-mails and decide whether to deliver or store the e-mail.

Figure 7:
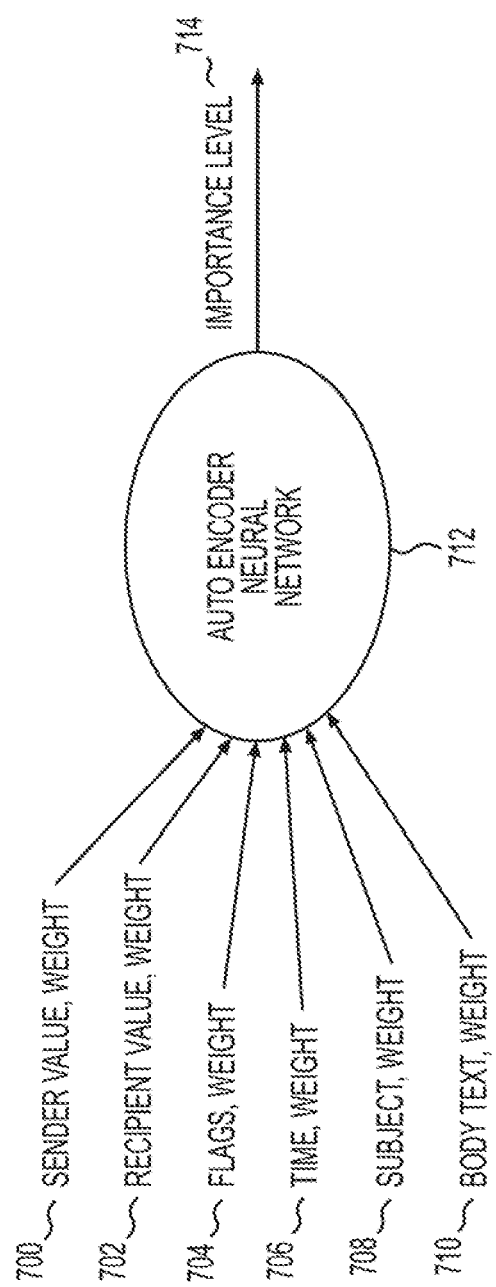
FIG. 7 illustrates an exemplary illustration of a neural network for filtering e-mail.

FIG. 7 illustrates an exemplary neural network for filtering e-mail. Although illustrated as a simplified neural network, it will be appreciated that the auto-encoder neural network 712 can include multiple inputs at differing levels. In addition, the inputs, weighting, and decisions of the neural network can be different for multiple users in the system because e-mails that have higher importance for one user may not be relevant for other users.

The neural network can have a plurality of inputs, such as the sender 700, the recipient 702, any flags 704 (e.g., the e-mail was marked as having high importance by a sender, a read receipt was requested by a sender, the recipient flagged the e-mail for follow-up, a flag to indicate that the recipient replied to the e-mail or a similar e-mail previously), the time the e-mail was sent 706, the subject 708, and the body text or keywords from the body text 710. Each input can be associated with a weight that defines the importance of the particular input. The weight of each factor can change based on the value of the factor and based on learning by the neural network. For example, a weight for a sender having a particular value of John Doe might initially be low, but if user frequently opens and reads messages from John Doe then the weight can be increased. As another example, the recipient value 702 can have a low weight if the user is included in a distribution list or if the user is only copied on the e-mail, a higher weight if the user is listed in the to line as the only recipient, and an even higher weight if the user is listed in the to line as a recipient along with a particular person, such as the user's supervisor.

The subject 708 and body text 710 can be based on extracted keywords, with the keywords being assigned a particular weight. If a user previously read or marked a particular e-mail as important, keywords from that e-mail can be extracted and provided as inputs with a higher weighting. For example, if a user previously read an e-mail relating to a meeting today regarding project ABC, the keywords or keyword phrases for "meeting today" and "project ABC" can be given a higher weighting. Any number of keywords can be identified and assigned a weight for use in the neural network 712.

In the event of a conflict among a plurality of factors, where some factors indicate the e-mail should be filtered and others indicate the e-mail should be delivered, the secure e-mail gateway can deliver the e-mail to avoid a user missing a potentially important e-mail. For example, assume a user defines or the system learns that all e-mail from a particular sender should be delivered. However, the user also has a rule that all e-mail sent between 1:00 AM and 5:00 AM should be filtered. If the particular sender sends an e-mail between 1:00 AM and 5:00 AM, the secure e-mail gateway can ignore the rule to filter e-mail sent during the defined timeframe and proceed with delivering the e-mail.

Additional factors include how many times a user opens or reads a particular e-mail message, the duration that a user reads a particular e-mail, whether the user marks an e-mail as a favorite or flags the message for follow-up, and the order in which a user read a message. When a user views all messages as equally important, the user may choose to view e-mails beginning with the oldest first or the newest first, and proceed chronologically. However, if a user selects and reads an e-mail out of sequence, the characteristics of that e-mail (e.g., sender, time, and keywords) can be given a higher weight because the user's actions indicate that similar e-mails are likely to be important to the user in the future.

Additional indicators of the importance of e-mail include factors indicating that the e-mail is part of a mass e-mail. For example, an automated e-mail sent from or to a distribution list can be weighted to lower their importance. However, if the e-mail originates from a particular sender, such as a recipient's supervisor or an executive of the company, the weighting of the sender can lead to marking the e-mail as important even when the e-mail is sent to a distribution list.

The weights for each input can be assigned with reference to a threshold value. For example, a weight of 0.5 can indicate a particular input falls in the middle range of importance, with increasingly higher weights indicating higher importance, and lower weights indicating less importance. The weights can be dynamically adjusted based on feedback from the system and from user interaction with particular e-mails.

The auto-encoder neural network 712 determines, based on the inputs and the associated weights, the overall importance level 714 for a particular e-mail message. The importance level 714 can be a numerical value within a range, where any value above a threshold will determine that the message should either be delivered or filtered. The importance level 714 can therefore be the summation of the inputs and weights for each input.

The neural network can continuously monitor and update its algorithm by changing the weight of inputs based on user interactions. For example, if a user repeatedly flags an e-mail relating to a particular agenda, as determined by contextual text searching of the e-mails, similar e-mails relating to the agenda can be given greater importance. Likewise, if a user repeatedly deletes e-mail from a particular sender or relating to a particular agenda, similar e-mails can be filtered as unimportant by reducing the weight given to that sender or contextual searches of the e-mail subject and/or body.

In one example, the outcome of the weighting factors can be a floating point value. A threshold can be defined that can distinguish e-mails as either important or not important, where values equal to or above the threshold imply that the mail is important while values below it imply a non-important mail. Using the sender of an e-mail as an example, the neural network can compare the relative importance of this particular sender compared to all other senders of all mails that the user has received. This relative importance can be determined from several factors, including how the user deletes mails from this sender compared to all other senders, how often the user flags e-mail from this sender compared to all other senders, and how much priority does the sender give an e-mail from this particular sender given that he/she has received several mails which are pending review.

The weight assigned to a particular feature can be predetermined by the user through a user interface or automatically established and updated. As discussed previously, the inputs to the learning algorithm can be the value of the feature and the weight assigned to that particular feature as discussed above, represented by $I_i = W_i * V_i$, where i=any value between 0 and the number of inputs; I=actual input to neuron, W=weight assigned to the input, and V=value assigned to the input. The output can be the sum of all inputs, with 0.7 representing an exemplary sum at which the e-mail will be considered important based on the inputs and assigned weights.

In one example, each time the user sends or receives a new mail, the importance of the e-mail can be calculated to create an observed value. Based on interactions by the user, the importance of the e-mail can then be reconsidered to create an expected value. For example, the expected value can consider whether the user deleted, flagged, read, or replied to the e-mail. The expected value can be compared with the actual value, and adjustments can be made to the initial weights used to calculate the actual value such that the actual value matches the expected value, or approaches the expected value.

A cost function can be defined as $C(w,b) = (1/2n)(\Sigma_x(y(x)-a)^2)$, where C is the cost for a given weight sum and threshold sum for all inputs, y(x) is the observed output, a is the expected output, and n is the number of training data elements. The algorithm can update to minimize C and therefore minimize the difference between the observed output and the expected output. The minimum cost can be derived using a gradient descent as follows: $\Delta C = \partial C / \partial v1 \Delta v1 + \partial C / \partial v2 \Delta v2$, where v1 and v2 can be weights and threshold, while C can be the cost which must be minimized.

Considering one variable at a time, let $\Omega C = \partial C/\partial v1$, then, $\Delta C = \Delta v * \Omega C$. Let $\Delta v = -\mu * \Omega C$. Therefore, $\Delta C = -\mu*(\Omega C)^2$. $\Delta C$ can therefore be negative which implies that it is moving towards decreasing the minimum. By taking small steps towards reaching in the direction which decreases the cost, the algorithm can reach the global minimum cost, which implies that there is very little difference between the actual and the observed outputs.

An example for the above may be as follows. An employee considers e-mail from a manager to be important and typically flags the e-mail or replies, and does not delete the e-mails. The employee's interactions increase the importance or relative value of e-mails from the manager compared to other senders. When the user manually requests only important e-mails or enters a low-power state, e-mail from the manager will be sent. If the employee moves to a different project and gets a new manager, e-mails from the new manager will initially be unimportant unless otherwise marked. However, with time, the user's interactions with e-mails from the new manager will train the algorithm to make those e-mails important, and likewise decreasing interaction with e-mails from the former manager will reduce the importance of those e-mails.

The above example relates to the sender of e-mail, but similar learning approaches can be used for other factors. For example, the subject and body of e-mail can be broken into tokens and the chi-square and Naive Bayes algorithms can be applied to determine if particular words or phrases are important based on the frequency of words occurring in important verse not important e-mails. Trivial words like articles (a, the, an) can be ruled out. The output of the Naive Bayes algorithm can be used as one of the inputs in the auto-encoder neural network.

Though some of the described methods have been presented as a series of steps, it should be appreciated that one or more steps can occur simultaneously, in an overlapping fashion, or in a different order. The order of steps presented is illustrative of the possibilities and those steps can be executed or performed in any suitable fashion. Moreover, the various features of the examples described here are not mutually exclusive. Rather any feature of any example described here can be incorporated into any other suitable example. It is intended that the specification and examples be considered as exemplary only, with a true scope and spirit of the invention being indicated by the following claims.

What is claimed is:

1. A method for providing e-mail, comprising:
   receiving, at a gateway server that controls access to an e-mail server, an indication that e-mail messages are available at an e-mail account associated with a first and second user device of a user;
   storing the new e-mail messages at the gateway server;
   transmitting e-mail notifications from the gateway server to each of the first and second user devices;
   receiving, at the gateway server in response to the e-mail notifications, a first indication of a first battery level in the first user device, and a second indication of a second battery level in the second user device, wherein the first and second indications include device identifiers of the first and second user devices, respectively;
   comparing the first and second battery levels to a threshold level;
   synchronizing e-mail with the first user device when the first battery level meets the threshold level;
   activating at the gateway server, when the second battery level is below the threshold level, a filtered mode for synchronizing e-mail with the second user device, the filtered mode transmitting a filtered portion of the available e-mail messages to the second user device;
   transmitting the unfiltered portion of the available e-mail messages to the second user device when the second battery level is above the threshold level; and
   deleting the stored e-mail messages from the gateway server based on transmitting the messages to both the first and second user devices.

2. The method of claim 1, wherein the indications of the first and second battery levels comprise a percentage of battery life remaining, and wherein the filtered portion of the available e-mail message is selected by a ranking engine, executing on the gateway server, that ranks each available e-mail message and filters the available e-mail messages based on their respective rankings.

3. The method of claim 1, further comprising receiving a first device identifier for the first user device and receiving a second device identifier for the second user device.

4. The method of claim 1, further comprising executing a neural network based on a plurality of factors to determine whether a new e-mail should be filtered or provided to the second user device during filtered mode.

5. The method of claim 4, further comprising updating weighting factors for inputs to the neural network based on a user's interaction with e-mail.

6. A non-transitory, computer-readable medium containing instructions executed by a processor to perform stages for delivering e-mail, the stages comprising:
   receiving, at a gateway server that controls access to an e-mail server, an indication that e-mail messages are available at an e-mail account associated with a first and second user device of a user;
   storing the new e-mail messages at the gateway server;
   transmitting e-mail notifications from the gateway server to each of the first and second user devices;
   receiving, at the gateway server in response to the e-mail notifications, a first indication of a first battery level in the first user device, and a second indication of a second battery level in the second user device, wherein the first and second indications include device identifiers of the first and second user devices, respectively;
   comparing the first and second battery levels to a threshold level;
   synchronizing e-mail with the first user device when the first battery level meets the threshold level;
   activating at the gateway server, when the second battery level is below the threshold level, a filtered mode for synchronizing e-mail with the second user device, the filtered mode transmitting a filtered portion of the available e-mail messages to the second user device;
   transmitting the unfiltered portion of the available e-mail messages to the second user device when the second battery level is above the threshold level; and
   deleting the stored e-mail messages from the gateway server based on transmitting the messages to both the first and second user devices.

7. The computer-readable medium of claim 6, wherein the indications of the first and second battery levels comprise a percentage of battery life remaining.

8. The computer-readable medium of claim 6, wherein the stages further comprise receiving a first device identifier for the first user device and receiving a second device identifier for the second user device.

9. The computer-readable medium of claim 6, wherein the stages further comprise executing a neural network based on a plurality of factors to determine whether a new e-mail should be filtered or provided to the second user device during filtered mode.

10. The computer-readable medium of claim 9, wherein the stages further comprise updating weighting factors for inputs to the neural network based on a user's interaction with e-mail.

11. A gateway server for controlling access to an e-mail server, wherein the gateway server:
   receives an indication that e-mail messages are available at an e-mail account associated with a first and second user device of a user;
   stores the new e-mail messages at the gateway server;
   transmits e-mail notifications from the gateway server to each of the first and second user devices;
   receives, in response to the e-mail notifications, a first indication of a first battery level in the first user device and a second indication of a second battery level in the second user device, wherein the first and second indications include device identifiers of the first and second user devices, respectively;
   compares the first and second battery levels to a threshold level;
   synchronizes e-mail with the first user device when the first battery level meets the threshold level;
   activates at the gateway server, when the second battery level is below the threshold level, a filtered mode for synchronizing e-mail with the second user device, the filtered mode transmitting a filtered portion of the available e-mail messages to the second user device;
   transmits the unfiltered portion of the available e-mail messages to the second user device when the second battery level is above the threshold level; and
   deletes the stored e-mail messages from the gateway server based on transmitting the messages to both the first and second user devices.

12. The system of claim 11, wherein the indications of the first and second battery levels comprise a low level or a high level.

13. The system of claim 11, wherein the gateway server further receives a command from the second user device to override the filtered mode.

14. The system of claim 11, wherein the gateway server further executes a neural network based on a plurality of factors to determine whether a new e-mail should be filtered or provided to the second user device during filtered mode.

* * * * *